United States Patent
Daigle et al.

(10) Patent No.: US 10,405,544 B2
(45) Date of Patent: *Sep. 10, 2019

(54) DISINFECTANT FORMULATION

(71) Applicant: LABORATOIRE M2, Sherbrooke (CA)

(72) Inventors: Francois Daigle, Canton de Hatley (CA); Ann Letellier, Massueville (CA); Sylvain Quessy, Sainte-Anne-de-Sorel (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/142,833

(22) Filed: Sep. 26, 2018

(65) Prior Publication Data

US 2019/0021316 A1    Jan. 24, 2019

Related U.S. Application Data

(63) Continuation-in-part of application No. 15/391,995, filed on Dec. 28, 2016, now Pat. No. 10,111,425, which is a continuation-in-part of application No. 15/055,044, filed on Feb. 26, 2016, now Pat. No. 9,609,864, which is a continuation-in-part of application No. 14/163,133, filed on Jan. 24, 2014, now Pat. No. 9,451,763, which is a continuation-in-part of application No. 12/420,688, filed on Apr. 8, 2009, now Pat. No. 8,691,292.

(60) Provisional application No. 61/043,317, filed on Apr. 8, 2008.

(51) Int. Cl.
  *A01N 25/02*    (2006.01)
  *A01N 31/08*    (2006.01)

(52) U.S. Cl.
  CPC .............. *A01N 31/08* (2013.01); *A01N 25/02* (2013.01)

(58) Field of Classification Search
  None
  See application file for complete search history.

(56) References Cited

U.S. PATENT DOCUMENTS

| | | |
|---|---|---|
| 3,947,570 A | 3/1976 | Pensak et al. |
| 3,983,252 A | 9/1976 | Buchalter |
| 4,414,128 A | 11/1983 | Goffinet |
| 5,403,587 A | 4/1995 | McCue et al. |
| 8,691,292 B2 | 4/2014 | Daigle |
| 2003/0083212 A1 | 5/2003 | Willard |
| 2005/0153857 A1 | 7/2005 | Sherry |
| 2005/0182142 A1 | 8/2005 | Kobayashi |
| 2008/0032908 A1 | 2/2008 | Kurtz |

FOREIGN PATENT DOCUMENTS

| | | |
|---|---|---|
| CA | 2371925 A1 | 12/2000 |
| CA | 2441730 A1 | 10/2002 |
| EP | 0948892 A1 | 10/1999 |
| JP | 2002511391 A | 4/2002 |
| JP | 2003012411 A | 1/2003 |
| JP | 2003551246 A | 10/2003 |
| KR | 20000023826 A | 4/2000 |
| WO | 9952360 A1 | 10/1999 |
| WO | 0179409 A1 | 10/2001 |
| WO | 0184936 A1 | 11/2001 |
| WO | 03037270 A2 | 5/2003 |
| WO | 2007133934 A1 | 11/2007 |

OTHER PUBLICATIONS

Kintzios, "Oregano: the genera Origanum and Lippia"; CRC Press, Aug. 2002, p. 277.

International Search Report of International Patent Application PCT/CA2009/000458; dated Jul. 13, 2009.

*Primary Examiner* — Susan T Tran
*Assistant Examiner* — William Craigo
(74) *Attorney, Agent, or Firm* — Benoit & Cote, Inc.; Mathieu Miron

(57) ABSTRACT

An aqueous disinfectant formulation comprising at least one phenolic compound of natural origin; a surfactant sufficient to form a solution or dispersion of the essential oil in an aqueous carrier; a solvent, and sufficient water to make 100 weight percent is described herein.

18 Claims, No Drawings

DISINFECTANT FORMULATION

CROSS REFERENCE TO RELATED APPLICATIONS

This application is filed under 37 CFR 1.53(b) as a continuation-in-part application. This application claims priority under 35USC § 120 of U.S. patent application Ser. No. 15/391,995 filed Dec. 28, 2016, which claims the benefit of U.S. patent application Ser. No. 15/055,044 filed Feb. 26, 2016, which claims the benefit of U.S. patent application Ser. No. 14/163,133 filed on Jan. 24, 2014, which claims the benefit of U.S. patent application Ser. No. 12/420,688 filed on Apr. 8, 2009, which claims the benefit of U.S. patent Provisional Application No. 61/043,317 filed on Apr. 8, 2008, the entire contents of which are incorporated by reference in their entireties.

FIELD OF THE INVENTION

The present invention broadly relates to disinfectant formulations comprising one or more phenolic compounds of natural origin. More specifically, but not exclusively, the present invention relates to formulations comprising one or more essential oils enriched in one or more phenolic compounds of natural origin suitable for disinfecting and cleaning large surface areas such as commonly encountered in agricultural settings, the formulations typically comprising one or more essential oils.

BACKGROUND OF THE INVENTION

In spite of modern improvements in hygiene and infection prevention, livestock health has become an increasingly important public health issue. This has been due in part to the fact that infections caused by viruses, bacteria and fungi have increased as a result of travel and global interconnections.

Pathogens such as bacteria, fungi, viruses, and bacterial spores are responsible for a plethora of human and animal ills, as well as contamination of food and biological and environmental samples. The first step in microbial infections of animals is generally attachment or colonization of skin or mucus membranes, followed by subsequent invasion and dissemination of the infectious microbe. The portals of entry of pathogenic bacteria are predominantly the skin and mucus membranes.

Virtually every intensive livestock producer accepts that effective disease prevention is key for maintaining a healthy enterprise. Over the years the improvement in and availability of vaccines has greatly assisted in the prevention of a large number of diseases. However, even a well vaccinated livestock can succumb under severe challenge. Moreover, since vaccines are not available for all the diseases to be prevented, producers have accepted that a well-planned and monitored bio-security program, coupled with an effective disinfection and vaccination program, is essential for maintaining the health of their stock.

Avian influenza is an infectious disease of birds caused by type A strains of the influenza virus. The disease, which was first identified in Italy more than 100 years ago, occurs worldwide. All birds are thought to be susceptible to infection with avian influenza, though some species are more resistant to infection than others. Domestic poultry, including chickens and turkeys are particularly susceptible to epidemics of rapidly fatal influenza.

Fifteen subtypes of influenza virus are known to infect birds, thus providing an extensive reservoir of influenza viruses potentially circulating in bird populations. To date, all outbreaks of the highly pathogenic form have been caused by influenza A viruses of subtypes H5 and H7. Recent research has shown that that viruses of low pathogenicity can, after circulating for sometimes short periods in a poultry population, mutate into highly pathogenic viruses.

The quarantining of infected farms and destruction of infected or potentially exposed flocks are standard control measures aimed at preventing spread to other farms and eventual establishment of the virus in a country's poultry population. Apart from being highly contagious, avian influenza viruses are readily transmitted from farm to farm by mechanical means, such as by contaminated equipment, vehicles, feed, cages, or clothing. Stringent sanitary measures on farms can, however, confer some degree of protection.

A great many of the current antimicrobial compositions, including sanitizers and disinfectants, contain antimicrobial agents which are not naturally occurring. Typical antimicrobial agents used in sanitizers and disinfectants include chemical disinfectants such as phenolic compounds, quaternary ammonium compounds, strong oxidizer, formaldehyde and halogen containing compounds. Such materials are not of natural origin (i.e. not found in nature) and are prepared through chemical processing and synthesis. A great many of these "synthetic" disinfectants cause undesirable effects on both the environment and on human health. The concept of formulating disinfectants, essentially involving the selection of a simple chemical disinfectant and enhancing its activity by adding other chemicals, evolved in the seventies.

The enhancement of the activity of a simple chemical disinfectant or combination of simple disinfectants to increase the spectrum of activity frequently involves the addition of additional chemical agents. Such additional chemical agents will generally have an effect on the pH and surface activity of the formulated product once in solution. It is well established that a number of simple disinfectants demonstrate their optimum activity at a specific pH (i.e. acidity or alkalinity). The ability of the disinfectant solution to make complete and even contact with the surface to be treated is also of great importance. This can generally be achieved by the addition of a surfactant or detergent to the formulation.

Disinfectants play a vital role in any biosecurity system, both in the process of terminal disinfection and in the ongoing hygiene maintenance. Apart from relatively minor changes and improvements in formulations, there has been little innovation in livestock disinfectant and large-surface disinfectant development for some fifteen to twenty years.

While some natural plant oils have been known since antiquity to have curative properties, the topical and oral benefits of natural plant oils have more recently been attributed to antimicrobial properties. A great many of the natural essential oils are derived from cajeput, cedarwood, citronella, clove, cypress, fir-needle, eucalyptus, garlic, lavender, lemon, lemongrass, marjoram, niaouli, onion, orange, oregano, patchouli, peppermint, rosemary, rosewood, tea tree, y-lang and vetivert. Of these natural essential oils, oregano oil, comprising a complex mixture of antimicrobial compounds, has been used as a reference for the comparison of the bactericidal action of other substances owing to its near ideal antibacterial properties. Oregano oil has been demonstrated as exerting a high degree of anti-fungal, anti-parasitic, anti-viral and antibacterial action. The phenolic flavenoids carvacol and thymol are two potent natural antiseptic agents encountered primarily in oregano oil.

Attempts have been made to formulate disinfectant solutions based upon essential oils. However, because of their hydrophobic nature, essential oils are not readily miscible in water. As a result, essential oils are often difficult to prepare in a form that will allow them to be readily incorporated into an aqueous solution.

U.S. Pat. No. 5,403,587 issued to McCue et al. on Apr. 4, 1995 discloses an antimicrobial composition that uses both a solvent and a surfactant to facilitate the formation of a homogeneous aqueous mixture of an essential oil. However, this composition is not suitable for disinfecting large surfaces such as commonly encountered in agricultural settings where the disinfectant solution is commonly prepared from a concentrate using the on-site water source.

The present invention refers to a number of documents, the content of which is herein incorporated by reference in their entirety.

SUMMARY OF THE INVENTION

The present invention relates to disinfectant formulations comprising one or more phenolic compounds of natural origin.

As broadly claimed, the present invention relates to aqueous formulations suitable for disinfecting and cleaning large surfaces and comprising one or more phenolic compounds of natural origin.

In an embodiment, the present invention relates to an aqueous disinfectant formulation comprising:
  at least one phenolic compound of natural origin;
  a surfactant in an amount sufficient to form a solution or dispersion of the phenolic compound in an aqueous carrier;
  a solvent;
  a sequestering agent; and
  sufficient water to make 100 weight percent.

In an embodiment, the present invention relates to an aqueous disinfectant formulation comprising:
  at least one phenolic compound of natural origin;
  a surfactant in an amount sufficient to form a solution or dispersion of the phenolic compound in an aqueous carrier;
  a solvent; and
  sufficient water to make 100 weight percent.

In an embodiment of the present invention, the phenolic compound of natural origin is an active ingredient commonly found in essential oils. In a further embodiment of the present invention, the phenolic compound is an active ingredient of oregano oil.

In an embodiment, the present invention relates to disinfectant formulations exhibiting antibacterial properties.

In an embodiment, the present invention relates to disinfectant formulations exhibiting antimicrobial properties.

In an embodiment, the present invention relates to an aqueous disinfectant formulation for denaturing biofilms.

In an embodiment, the present invention relates to disinfectant formulations exhibiting antiviral properties.

In an embodiment, the present invention relates to disinfectant formulations exhibiting antifungal properties.

In an embodiment, the present invention relates to a disinfectant formulation comprising a homogeneous aqueous solution.

In an embodiment, the present invention relates to an aqueous disinfectant formulation generating a foam when applied to a surface to be disinfected. The foam adheres to the surface to be disinfected for a time sufficient to ensure eradication of the non-indigenous and/or pathogenic bacterial population.

In an embodiment, the present invention relates to an aqueous disinfectant formulation generating a foam when applied to a surface to be disinfected. The foam adheres to the surface to be disinfected for a time sufficient to ensure eradication of the non-indigenous and/or pathogenic microbial population.

In an embodiment, the present invention relates to an aqueous disinfectant formulation generating a foam when applied to a surface to be disinfected. The foam adheres to the surface to be disinfected for a time sufficient to ensure eradication of the non-indigenous pathogenic and/or viral population.

In an embodiment, the present invention relates to an aqueous disinfectant formulation generating a foam when applied to a surface to be disinfected. The foam adheres to the surface to be disinfected for a time sufficient to ensure eradication of the non-indigenous and/or pathogenic fungal population.

The disinfectant formulations of the present invention can be dispensed using any suitable application means. In an embodiment, the disinfectant formulations of the present invention are applied to a surface using a foamer.

In a further embodiment, the present invention relates to biodegradable disinfectant formulations.

Finally, the present invention relates to disinfectant formulations retaining their properties when diluted with hard water.

The foregoing and other objects, advantages and features of the present disclosure will become more apparent upon reading of the following nonrestrictive description of illustrative embodiments thereof, given by way of example only.

DETAILED DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "hard water" as used herein refers to water having a high concentration of dissolved minerals and solids.

The term "natural origin" as used herein refers to phenolic compounds that exist or are produced in nature. Such phenolic compounds can be extracted or isolated from their natural environment by any suitable means. Of course, such phenolic compounds can also be synthetically produced by the hand of man. Such synthetic equivalents are within the definition of "natural origin".

Antimicrobial agents that are useful in the present invention are the so-called "natural" antimicrobial actives, referred to as natural essential oils. These actives derive their names from their natural occurrence in plants. Essential oils include oils derived from herbs, flowers, trees, and other plants. Such oils are typically present as tiny droplets between the plant's cells, and can be extracted by several methods known to those of skill in the art (e.g., steam distillation, enfleurage (i.e., extraction using fat(s)), maceration, solvent extraction, or mechanical pressing). Essential oils are typically named by the plant or vegetable in which the oil is found. For example, rose oil or peppermint oil is derived from rose or peppermint plants, respectively. Non-limiting examples of essential oils that can be used in the context of the present invention include oils of anise, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea origanum oil, Hydastis carradensis oil, Berberidaceae daceae oil, Ratanhiae and Curcuma longa oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Other essential oils known to those of skill in the art are also contemplated as being useful within the context of the present invention (e.g., International Cosmetic Ingredient Dictionary, 10th edition, 2004, which is incorporated by reference). Also included in this class of essential oils are the key chemical components of the plant oils that have been found to provide the antimicrobial benefit (e.g. phenolic compounds).

The phenolic compounds of natural origin as used in the present invention can be synthetically made by known methods within the capacity of a skilled technician, or can be obtained from plant oil extracts. In an embodiment of the present invention, the phenolic compounds of natural origin are obtained from plant extracts. In a further embodiment of the present invention, the phenolic compounds of natural origin are commercially available. In yet a further embodiment of the present invention, the phenolic compounds of natural origin comprise carvacrol and thymol.

In an embodiment, the disinfectant formulations of the present invention comprise thymol, carvacrol or mixtures thereof. In a further embodiment, the disinfectant formulations of the present invention comprise one or more natural essential oils enriched in thymol, carvacrol or mixtures of thymol and carvacrol.

In an embodiment, the disinfectant formulations of the present invention further comprise a surfactant. A surfactant operative herein comprises a water soluble or water dispersible nonionic, anionic, cationic, or an amphoteric compound. In a further embodiment, the disinfectant formulations of the present invention comprise one or more of the conventional anionic surfactants known in the art. A representative listing of surfactants and properties thereof is detailed in Remington's Pharmaceutical Sciences, 17th edition (Mack Publishing Company). Non-limiting examples of surfactants according to an embodiment of the present invention include sodium lauryl sulfate, sorbitan stearate, sorbitan esters, sodium laureth sulfate, sarkosyl, cocamidopropyl betaine (CAPB), sodium lauryl ether sulfonate, alkyl benzene sulfonates, nonylphenol ethoxylate and ether ethoxylate. It is appreciated that one or more additional surfactants may be included in the disinfectant formulations of the present invention. A surfactant (surface active agent) is generally intended to refer to a substance which when dissolved in water, or other aqueous system, reduces the surface or interfacial tension between it and another substance or material. In an embodiment of the present invention, the surfactant aids in the dispersion or emulsification of the essential oils within the aqueous carrier. According to an embodiment, the dispersion is not necessarily and homogenous dispersion. The dispersion may necessitate agitation and/or shaking prior to use. According to another embodiment, the dispersion is a homogenous dispersion. In a further embodiment of the present invention, the anionic surfactant aids in braking down the structure of biofilms through denaturation. In yet a further embodiment of the present invention, the surfactant allows for the creation of a "foaming effect" when the disinfectant solution is applied to a surface to be treated. The creation of a foam allows for the disinfectant solutions to remain in contact with the surface to be treated for longer periods of time. In yet a further embodiment, the surfactant acts as a "wetting" agent. Wetting agents typically reduce the surface tension of the water molecules, allowing for a greater spreading of the solution and a deeper penetration into small crack and crevices of the surface to be treated.

Phenolic compounds (e.g. carvacrol, thymol) are typically not sufficiently soluble in an aqueous medium. The disinfectant formulations of the present invention thus typically comprise a solvent. The solvents may be hydrophilic, hydrophobic or amphiphilic in nature. In an embodiment, the disinfectant formulations of the present invention comprise an amphiphilic solvent. Amphiphilic solvents are capable of solubilizing the phenolic compounds of natural origin and/or the essential oil(s) in the aqueous carrier. Non-limiting examples of solvents according to an embodiment of the present invention include methanol, ethanol, hexadecane, propylene glycol, propylene glycol n-butyl ether, propylene glycol methyl ether acetate, propylene glycol methyl ether, dipropylene glycol n-propyl ether, ethylene glycol methyl ether and hexylene glycol. The addition of a significant amount of solvent to the disinfectant solutions of the present invention, allows for the solutions to be used at temperatures slightly inferior to OoC. It is well within the capacity of a skilled technician to determine such amounts of solvent.

Since the disinfectant formulations are typically prepared on site from mixtures of ingredients in concentrated solution, tap water is used for dilution. Tap water generally has a certain amount of hardness. Since the presence of dissolved minerals (e.g. $Ca^{++}$, $Mg^{++}$) may adversely affect the performance and properties of the disinfectant formulation, a sequestering agent is included in the formulation to chelate the dissolved minerals in the form of a water soluble complex. Sequestering agents are well known in the art. Non-limiting examples include ethylene diamine tetraacetic acid (EDTA) sodium salt, sodium gluconate, sodium citrate, trisodium ethylenediamine disuccinate, citric acid, trisodium NTA, sodium phosphate and sodium choleate. Sequestering agents typically prevent the dissolved minerals from binding to the surfactant molecules. Moreover, sequestering agents may remove minerals from the surface to be disinfected.

In an embodiment, the disinfectant formulations of the present invention comprise one or more phenolic compounds of natural origin. In an embodiment of the present invention, the phenolic compounds are selected from the group consisting of thymol and carvacrol. In a further embodiment, the disinfectant formulations of the present invention comprise carvacrol. In a further embodiment, the disinfectant formulations of the present invention comprise thymol. In a further embodiment, the disinfectant formulations of the present invention comprise carvacrol and thymol. In a particular embodiment, the disinfectant formulations of the present invention comprise 0.18% (w/w) thymol.

Phenolic compounds typically have an associated pungent odor severely impeding large-scale applications. In an embodiment, the disinfectant formulations of the present invention may thus further comprise one or more agents having the dual function of further enhancing the disinfectant properties of the formulations while imparting a more pleasant odor thereto. In yet a further embodiment of the present invention, the disinfectant formulations of the present invention may further comprise one or more agents imparting a pleasant odor thereto (fragrance agent). Non-limiting examples of agents imparting a pleasant odor and/or enhancing the disinfectant properties comprise carvacrol, cymene, cineol, eugenol, thymol, menthol, citral and limonene. Further suitable examples of such agents are within the capacity of a skilled technician.

The disinfectant formulations of the present invention may optionally include a wide range of additional ingredients non-limiting examples of which include colorants and pH adjusting agents. Such additional ingredients are within the capacity of a skilled technician. The colorant may be a dye, a pigment, a biological pigment, an ink, a food coloring. In embodiments, the colorant may help identifying a surface as having been treated with the composition of the present invention. Examples of colorants include but are not limited to FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 3—Erythrosine, E127 (pink shade, commonly used in glacé cherries); FD&C Red No. 40—Allura Red AC, E129 (red shade); FD&C Yellow No. 5—Tartrazine, E102 (yellow shade); FD&C Yellow No. 6—Sunset Yellow FCF, E110 (orange shade); E104: Quinoline Yellow; E122: Carmoisine; E124: Ponceau 4R; E131: Patent Blue V; E142: Green S; Annatto (E160b), a reddish-orange dye made from the seed of the achiote; Betanin (E162) extracted from beets; Butterfly pea, a blue food dye; Caramel coloring (E150a-d), made from caramelized sugar; Chlorophyllin (E140), a green dye made from chlorella algae; Elderberry juice; Lycopene (E160d); Carmine (E120), a red dye derived from the cochineal insect, Dactylopius coccus; Pandan (Pandanus amaryllifolius), a green food coloring; Paprika (E160c), Turmeric (curcuminoids, E100), Saffron (carotenoids, E160a). Preferably the dye is blue.

The colorant may be used in any suitable concentration, for example at concentrations of about 0.00005% to about 15% w/w, or from about 0.0005% to about 15% w/w, or from about 0.005% to about 15% w/w, or from about 0.05% to about 15% w/w, or from about 0.01% to about 15% w/w, or from about 0.1 to about 15% w/w, or from about 0.25 to about 15% w/w, or from about 0.5% to about 15% w/w, or from about 1% to about 15%, or from about 5% to about 15%, or from about 10% to about 15%, about 0.00005% to about 10% w/w, or from about 0.0005% to about 10% w/w, or from about 0.005% to about 10% w/w, or from about 0.05% to about 10% w/w, or from about 0.01% to about 10% w/w, or from about 0.1 to about 10% w/w, or from about 0.25 to about 10% w/w, or from about 0.5% to about 10% w/w, or from about 1% to about 10%, or from about 5% to about 10%, about 0.00005% to about 5% w/w, or from about 0.0005% to about 5% w/w, or from about 0.005% to about 5% w/w, or from about 0.01% to about 5% w/w, or from about 0.05% to about 5% w/w, or from about 0.1 to about 5% w/w, or from about 0.25 to about 5% w/w, or from about 0.5% to about 5% w/w, or from about 1% to about 5%, about 0.00005% to about 1% w/w, or from about 0.0005% to about 1% w/w, or from about 0.005% to about 1% w/w, or from about 0.01% to about 1% w/w, or from about 0.1 to about 1% w/w, or from about 0.25 to about 1% w/w, or from about 0.5% to about 1% w/w, about 0.00005% to about 0.25% w/w, or from about 0.0005% to about 0.25% w/w, or from about 0.005% to about 0.25% w/w, or from about 0.01% to about 0.25% w/w, or from about 0.1 to about 0.25% w/w, or about 0.00005% to about 0.1% w/w, or from about 0.0005% to about 0.1% w/w, or from about 0.005% to about 0.1% w/w, or from about 0.01% to about 0.1% w/w, or about 0.00005% to about 0.1% w/w, or from about 0.0005% to about 0.1% w/w, or from about 0.005% to about 0.1% w/w, or from about 0.01% to about 0.1% w/w, or about 0.00005% to about 0.01% w/w, or from about 0.0005% to about 0.01% w/w, or from about 0.005% to about 0.01% w/w, or from about 0.00005% to about 0.005% w/w, or from about 0.0005% to about 0.005% w/w.

As used herein, the term "pH adjusting agent" is intended to mean is a compound that will change the pH of a solution of the present invention by making it more alkaline or acidic, as may be required. Examples include acids, bases, as well as buffering agents.

According to some embodiments, in the first stage of cleaning, the identify the pollutant to be removed needs to be ascertained. There are two basic categories for pollutants: organic and inorganic. Organic pollutants are those based on carbon, such as oils, fats, carbohydrates, proteins, molds, yeasts, and animal waste. Generally, they must be removed with an alkaline cleaner (pH>7). Inorganic pollutants are substances that are not organic (carbon-based), such as deposits of tartar and lime, rust, corrosion and oxidation. These types of fouling are usually removed by an acid cleaner (pH<7). Therefore, the pH of the formulations of the present invention may be from about 1 to about 11, or from about 2 to about 11, or from about 3 to about 11, or from about 4 to about 11, or from about 5 to about 11, or from about 6 to about 11, or from about 7 to about 11, or from about 8 to about 11, or from about 9 to about 11, or from about 10 to about 11, or from about 1 to about 10, or from about 2 to about 10, or from about 3 to about 10, or from about 4 to about 10, or from about 5 to about 10, or from about 6 to about 10, or from about 7 to about 10, or from about 8 to about 10, or from about 9 to about 10, or from about 1 to about 9, or from about 2 to about 9, or from about 3 to about 9, or from about 4 to about 9, or from about 5 to about 9, or from about 6 to about 10, or from about 7 to about 9, or from about 8 to about 9, or from about 1 to about 8, or from about 2 to about 8, or from about 3 to about 8, or from about 4 to about 8, or from about 5 to about 8, or from about 6 to about 8, or from about 7 to about 8, or from about 1 to about 7, or from about 2 to about 7, or from about 3 to about 7, or from about 4 to about 7, or from about 5 to about 7, or from about 6 to about 7, or from about 1 to about 6, or from about 2 to about 6, or from about 3 to about 6, or from about 4 to about 6, or from about 5 to about 6, or from about 1 to about 5, or from about 2 to about 5, or from about 3 to about 5, or from about 4 to about 5, or from about 1 to about 4, or from about 2 to about 4, or from about 3 to about 4, or from about 1 to about 3, or from about 2 to about 3, or from about 1 to about 2. Preferably, the pH may be from about 5 to about 6, also preferably, the pH may be from about 8 to 9.

According to an embodiment, the pH adjusting agent is chosen from citric acid, lactic acid, hydrochloric acid, boric acid, acetic acid, sodium hydroxide, potassium hydroxide, sulfuric acid, calcium carbonate ($CaCO_3$), ammonium carbonate, ammonium bicarbonate, ammonium citrate, sodium citrate, magnesium carbonate, sodium carbonate, mono, di and/or trisodium phosphate, mono, di and/or tripotassium phosphate, Tris(hydroxymethyl) aminomethane (TRIS), amino acids and zwitterions, such as glycine, 2-amino-2methyl-1,3-propanediol (AMPD), N-(1,1-Dimethyl-2-hydroxyethyl)-3-amino-2-hydroxypropanesulfonic acid (AMPSO), N-Glycylglycine (Gly-Gly), 4-(2-hydroxyethyl) piperazine-1-propanesulfonic acid (EPPS or HEPPS), 3-(cyclohexylamino)-1-propanesulfonic acid (CAPS), 3-(cyclohexylamino)-2-hydroxy-1-propanesulfonic acid (CAPSO), 2-(cyclohexylamino)ethanesulfonic acid (CHES), N,N-bis[2-hydroxyethyl]-2-aminoethanesulphonic acid (BES), (2-[2-hydroxy-1,1-bis(hydroxymethyl)ethylamino] ethanesulphonic acid) (TES), 2-(N-morpholino)ethanesulfonic acid (MES), N-[Tris(hydroxymethyl)methyl]glycine (Tricine); N-Tris(hydroxymethyl)methyl-3-aminopropanesulfonic acid (TAPS) and 3-N-Morpholino propanesulfonic acid (MOPS), piperazie-N, N'-bis[2-hydroxypropanesulphonic]acid (POPSO), and combinations thereof. According to a preferred embodiment, the pH adjusting agent is citric acid. According to another preferred embodiment, the pH adjusting agent is lactic acid.

The role of the pH adjusting agent is to adjust the acidity or alkalinity of the composition of the present invention. According to an embodiment, the composition of the present invention may comprise from about 0.01% to about 5% (w/w), or from about 0.01% to about 4%, or from about 0.01% to about 3%, or from about 0.01% to about 2%, or from about 0.01% to about 1%, or from about 0.01% to about 0.75%, or from about 0.01% to about 0.5%, or from about 0.01% to about 0.25%, or from about 0.01% to about 0.1%, or from about 0.01% to about 0.075%, or from about 0.01% to about 0.05%, or from about 0.01% to about 0.025%, or from about 0.01% to about 0.02%, or from about 0.01% to about 0.015%, or 0.015% to about 5% (w/w), or from about 0.015% to about 4%, or from about 0.015% to about 3%, or from about 0.015% to about 2%, or from about 0.015% to about 1° A, or from about 0.015% to about 0.75%, or from about 0.015% to about 0.5%, or from about 0.015% to about 0.25%, or from about 0.015% to about 0.1%, or from about 0.015% to about 0.075%, or from about 0.015% to about 0.05%, or from about 0.015% to about 0.025%, or from about 0.015% to about 0.02%, or 0.02% to about 5% (w/w), or from about 0.02% to about 4%, or from about 0.02% to about 3%, or from about 0.02% to about 2%, or from about 0.02% to about 1° A, or from about 0.02% to about 0.75%, or from about 0.02% to about 0.5%, or from about 0.02% to about 0.25%, or from about 0.02% to about 0.1%, or from about 0.02% to about 0.075%, or from about 0.02% to about 0.05%, or from about 0.02% to about 0.025%, or 0.025% to about 5% (w/w), or from about 0.025% to about 4%, or from about 0.025% to about 3%, or from about 0.025% to about 2%, or from about 0.025% to about 1%, or from about 0.025% to about 0.75%, or from about 0.025% to about 0.5%, or from about 0.025% to about 0.25%, or from about 0.025% to about 0.1%, or from about 0.025% to about 0.075%, or from about 0.025% to about 0.05%, or 0.05% to about 5% (w/w), or from about 0.05% to about 4%, or from about 0.05% to about 3%, or from about 0.05% to about 2%, or from about 0.05% to about 1%, or from about 0.05% to about 0.75%, or from about 0.05% to about 0.5%, or from about 0.05% to about 0.25%, or from about 0.05% to about 0.1%, or from about 0.05% to about 0.075%, or 0.075% to about 5% (w/w), or from about 0.075% to about 4%, or from about 0.075% to about 3%, or from about 0.075% to about 2%, or from about 0.075% to about 1%, or from about 0.075% to about 0.75%, or from about 0.075% to about 0.5%, or from about 0.075% to about 0.25%, or from about 0.075% to about 0.1%, or 0.1% to about 5% (w/w), or from about 0.1% to about 4%, or from about 0.1% to about 3%, or from about 0.1% to about 2%, or from about 0.1% to about 1%, or from about 0.1% to about 0.75%, or from about 0.1% to about 0.5%, or from about 0.1% to about 0.25%, or 0.25% to about 5% (w/w), or from about 0.25% to about 4%, or from about 0.25% to about 3%, or from about 0.25% to about 2%, or from about 0.25% to about 1%, or from about 0.25% to about 0.75%, or from about 0.25% to about 0.5%, or 0.5% to about 5% (w/w), or from about 0.5% to about 4%, or from about 0.5% to about 3%, or from about 0.5% to about 2%, or from about 0.5% to about 1%, or from about 0.5% to about 0.75%, or 0.75% to about 5% (w/w), or from about 0.75% to about 4%, or from about 0.75% to about 3%, or from about 0.75% to about 2%, or from about 0.75% to about 1%, or 1% to about 5% (w/w), or from about 1% to about 4%, or from about 1% to about 3%, or from about 1% to about 2%, or 2% to about 5% (w/w), or from about 2% to about 4%, or from about 2% to about 3%, or 3% to about 5% (w/w), or from about 3% to about 4%, or 4% to about 5% (w/w) of a pH adjusting agent. The preferred range over which it may be used is from about 1% to about 5% (w/w) in concentrated form of the present invention, or about 0.01% to about 0.05% (w/w).

The disinfectant formulations of the present invention may be applied onto a surface to be disinfected (i.e. cleaned) by means of a variety of spraying techniques. In an embodiment, the disinfectant formulations of the present invention are applied using a diffuser or a mist blower. Alternatively, the disinfectant formulations of the present invention can also be formulated into aerosol formulations. Further means of applying the disinfectant solutions of the present invention are within the capacity of a skilled technician. The disinfectant formulations of the present invention can either be applied directly or can be diluted prior to application. Due to the substantially non-corrosive nature of the disinfectant formulations of the present invention, the formulations can be readily applied without undue damage to the existing physical structure (i.e. surface).

In an embodiment, the disinfectant formulations of the present invention comprise one or more essential oils enriched in thymol and/or carvacrol. Thymol and carvacrol are naturally occurring disinfectants which are readily degraded in the environment. As such, there is little or no accumulation in the environment or in living organisms, even following repeated application of the disinfectant formulations of the present invention.

Formulations of the present invention can include any number of combinations of ingredients discussed throughout this specification (e.g., phenolic compounds of natural origin, essential oils, surfactants, solvents, sequestering agents, water, etc.). It is also contemplated that that the concentrations of the ingredients can vary. In non-limiting embodiments, for example, the formulations may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.6700%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the ingredients mentioned throughout the specification and/or claims. In non-limiting aspects, the percentage can be calculated by weight or volume of the total composition. A person of ordinary skill in the art would understand that the concentrations can vary depending on the desired effect of the formulation and/or on the product into which the formulation is incorporated into.

EXPERIMENTAL

Disinfectant Solutions

Chemical and Physical Characteristics of the Disinfectant Solutions

The sequestering agent (sodium citrate) was first dissolved in a predetermined amount of water and stirred until dissolution. Glycol ether PM (solvent), thymol, origanum oil and optionally citral (fragrance) were then added and stirred until dissolution. Surfactant (Sodium Lauryl Sulfate) and additional water were then added and stirred until dissolution to provide a 100 wt. % formulation. The final formulation was stirred until a homogeneous solution was obtained. Formulation 1, obtained from Formulation 2 by means of dilution with water (1:100), is considered a "ready to use" formulation.

|   | Thymol Crystal | Origanum Oil/Citral | Sequestrant | Surfactant | Solvent | pH |
|---|---|---|---|---|---|---|
| A | 0.18 | 0.04 | 0.01 | 0.12 | — | 6.9 |
| B | 0.18 | 0.04 | 0.01 | — | 0.18 | 6.7 |
| C | 0.18 | 0.04 | — | 0.12 | 0.18 | 6.5 |
| 1 | 0.18 | 0.04 | 0.01 | 0.12 | 0.18 | 6.5 |
| D | 18 | 4 | 1 | 12 | — | 8.1 |
| E | 18 | 4 | 1 | — | 18 | 7.9 |
| 2 | 18 | 4 | 1 | 12 | 18 | 8.8 |
| 3 | 0.18 | 0.03 | 0.09 | 0.12 | 0.76 | 8.0 |
| 4 | 6 | 1 | 3 | 4 | 25 | 8.2 |

|   | Solubility in Water | Stability | Foaming Effect | Foaming Effect in Hard Water |
|---|---|---|---|---|
| A | NO | NO | YES | YES |
| B | NO | NO | NO | YES |
| C | YES | YES | YES | NO |
| 1 | YES | YES | YES | YES |
| D | NO | NO | YES | n/a |
| E | NO | NO | NO | n/a |
| 2 | YES | YES | YES | n/a |
| 3 | YES | YES | YES | YES |
| 4 | YES | YES | YES | n/a | n/a: Not applicable this formula requires dilution before use

As illustrated hereinabove, the formulations are first formulated as a "concentrate" (Formulations 2 and 4), dilution of which provides for the preparation of Formulations 1 and 3. Formulations A, B, C, D, E, 1 and 2 comprise Origanum Oil/Citral (3:1). Formulations 3 and 4 do not comprise any fragrance (citral). The formulations have a pH ranging from about 6 to about 9. Dilution using hard water did not affect the characteristics of the formulation which is indicative of the efficacy of the sequestering agent.

Biological Efficacy of selected Phenolic Compounds and Essential Oils

The minimum concentration at which a total antimicrobial activity could be observed was determined for selected phenolic compounds of natural origin and selected essential oils using the AOAC method 955.15 ("Phenol Coefficient Method") with minor modifications. The results are indicative of the excellent antimicrobial activity of both thymol and carvacrol.

| Antimicrobial Agent | Minimal Concentration (v/v %) |
|---|---|
| Thymol | 0.07 |
| Carvacrol | 0.07 |
| Eugenol | 0.4 |
| Citral | >1% |
| Thyme oil | 0.3 |
| Origanum oil | 0.2 |
| Eucalyptus oil | >1% |
| Lemon oil | >1% |

Different concentrations of essential oils and phenolic compounds of natural origin were incorporated into composition F (see table herein below) and inoculated with a 0.05% bacterial suspension of *Staphylococcus aureus* (ATCC 6538; concentration of about 8 logs). After a contact time of 10 minutes, 0.1 ml of the inoculated solution was transferred to a broth culture with neutralizing (Difco 268110) and incubated over a period of 72 hours at 37° C. The presence of turbidity in the broth culture is indicative of the survival of the microorganism.

Quantitative Microbial Reduction Assay

The antimicrobial activity for selected formulations of the present invention was determined. Several formulations comprising a phenolic compound of natural origin or an essential oil (0.18%) were tested to determine their effectiveness in reducing the load of *Staphylococcus aureus* (ATCC 6538). The solutions were prepared from a concentrate and diluted with water (1:100). The results are indicative of the high efficiency of Formulations 5, 6 and 7 in reducing the load of *Staphylococcus aureus*.

|   | Antimicrobial Agent (w/w) | Sequestrant (w/w) | Surfactant (w/w) | Solvent (w/w) | Log Reduction |
|---|---|---|---|---|---|
| F | — | 0.01 | 0.12 | 0.18 | 0.60 |
| 5 | Thymol | 0.01 | 0.12 | 0.18 | 7.63 |
| 6 | Carvacrol | 0.01 | 0.12 | 0.18 | 7.63 |
| G | Eugenol | 0.01 | 0.12 | 0.18 | 2.50 |
| H | Citral | 0.01 | 0.12 | 0.18 | 2.04 |
| I | Thyme oil | 0.01 | 0.12 | 0.18 | 3.06 |
| 7 | Origanum oil | 0.01 | 0.12 | 0.18 | 7.63 |
| J | Eucalyptus oil | 0.01 | 0.12 | 0.18 | 0.71 |
| K | Lemon oil | 0.01 | 0.12 | 0.18 | 0.64 |

Different formulations of the present invention were inoculated with 0.05% of a bacterial culture of *Staphylococcus aureus* (ATCC 6538) freshly incubated over a period of 48 hours at 37° C. in an optimal growth medium. After a contact time of 10 minutes, 0.1 ml of the inoculated solution was seeded at different dilutions on TSA agar (Difco 255320) with neutralizing to determine the residual microbial load. The log reduction was determined by calculating the logarithm of the residual charge obtained with the reference formulation (i.e. water) and comparing it with the residual charge obtained using any of the formulations comprising either a phenolic compound or an essential oil.

Biological Efficacy of Formulation 1 on selected Microorganisms

The disinfectant formulations of the present invention exhibit a broad spectrum of activity on a variety of microorganisms. As shown hereinbelow, the efficacy of Formulation 1 against a variety of microorganisms was determined.

| Activity | Standard Method | Group of Microorganisms | Microorganisms | 1 |
|---|---|---|---|---|
| Bactericidal | AOAC[1] (Dilution Test) | Bacteria Gram − | *Salmonella cholerasuis* | Pass |
|  |  | Bacteria Gram + | *Staphylococcus aureus* | Pass |
| Fungicide | AOAC Fungicidal Activity Test | Fungus | *Trichophyton mentagrophytes* | Pass |
| Virucidal | ASTM[2] Efficacy of Virucidal Agents | Virus | Influenza A | Pass |

[1]Association of Analytical Communities,
[2]American Society for Testing and Materials Toxicity of the Disinfectant Formulations Toxicity tests ($LD_{50}$) were performed on selected ingredients of the disinfectant formulations of the present invention. Formulation 1 was determined as having a $LD_{50}$ of >15 g/Kg (substantially non-toxic).

| Ingredient | $LD_{50}$ Oral-rat | Specification |
|---|---|---|
| Thymol | 980 mg/kg | USP, FCC |
| Origanum oil | 1850 mg/kg | USP, FCC |
| Citral | 4960 mg/kg | Oxford University |
| Sodium Citrate | >8 g/kg | USP, FCC |
| Sodium Lauryl Sulfate | 1288 mg/kg | USP, FCC |
| Glycol Ether PM | 5 210 mg/kg | WHMIS |

Demonstration that All Types of Surfactants can be Used in the Disinfectant Formulation of the Present Invention Surfactants can be grouped by the charge characteristics of their polar head groups. The four groups are:

1. Anionic: Negative charge on the polar head group. These include surfactants like sulfates, sulfonic acids and carboxylic acids.

2. Cationic: Positive charge on the polar head group. These include surfactants like amines and Quaternized Ammonium Compounds (Quats).

3. Amphoteric: Can have both positive and negative charge. Primarily used as secondary surfactants. These include betaines and imidazolium compounds.

4. Non-ionic: No specific charge. By far the most frequently used surfactants. These include alcohols, alkanolamides, esters and amine oxides.

The antimicrobial efficacy of the compositions of the present invention is evaluated with all types of surfactants. The different compositions tested differ only for the surfactant. All compositions are based on the general formula presented in Table 1. The different surfactants tested are presented in Table 2. The surfactants were tested at a concentration of 0.12% (w/w) and/or 0.35% (w/w).

TABLE 1

| General formula of compositions 1 to 68 | |
|---|---|
| Ingredient | % (w/w) |
| Thymol | 0.23 |
| Surfactant | 0.12-0.35 |
| Solvent | 0.9 |
| Sequestrant | 0.09 |
| Water | Q.S. |

TABLE 2

| Surfactants tested in compositions 1 to 68 | | | | |
|---|---|---|---|---|
| # | Type | Chemical group | INCI Name | # CAS |
| 1 | Anionic | Alpha Sulfo Methyl Ester | Sodium Methyl 2-Sulfolaurate (and) Disodium 2-Sulfolaurate | 149458-07-1 |
| 2 | Anionic | Diphenyl Oxide Disulfonate | Sodium Dodecyl Diphenyl Ether Disulfonate | 119345-04-9 |
| 3 | Anionic | Diphenyl Oxide Disulfonate | Sodium Decyl Diphenyl Oxide Disulfonate | 6445-71-3 |
| 4 | Anionic | Dodecylbenzene Sulfonic Acid & Salts | Sodium Dodecylbenzenesulfonate | 68081-81-2 |

TABLE 2-continued

Surfactants tested in compositions 1 to 68

| # | Type | Chemical group | INCI Name | # CAS |
|---|------|----------------|-----------|-------|
| 5 | Anionic | Dodecylbenzene Sulfonic Acid & Salts | Dodecylbenzene Sulfonic Acid | 68584-22-5 |
| 6 | Anionic | ether carboxylate | Capryleth-9 carboxylic acid/ hexeth-4 carboxylic acid | 53563-70-5 and 105391-15-9 |
| 7 | Anionic | ether carboxylate | Glycolic Acid Ethoxylate Lauryl Ether | 27306-90-7 |
| 8 | Anionic | Isethionate | Sodium Cocoyl Isethionate | 61789-32-0 |
| 9 | Anionic | Lauryl Ether Sulfates | Sodium lauryl ether sulfate | 9004-82-4 |
| 10 | Anionic | Lauryl Sulfates | Sodium Lauryl Sulfate | 151-21-3 |
| 11 | Anionic | Lauryl Sulfates | Triethanolamine Lauryl Sulfate | 90583-18-9 |
| 12 | Anionic | Lauryl Sulfates | Magnesium Lauryl Sulfate | 3097-08-3 |
| 13 | Anionic | Phosphate Esters | Nonoxynol-10 Phosphate | 51609-41-7 |
| 14 | Anionic | Phosphate Esters | Deceth 4 Phosphate | 68921-24-4 |
| 15 | Anionic | Phophanates | Amino tri (methylene phosphonic acid) pentasodium salt, Na5ATMP | 20592-85-2 |
| 16 | Anionic | Phophanates | 1-Hydroxyethylidene-1,1,-diphosphonic acid | 2809-21-4 |
| 17 | Anionic | Sarcosinate | Sodium Lauroyl Sarcosinate | 137-16-6 |
| 18 | Anionic | Sulfosuccinates | Disodium Laureth Sulfosuccinate | 68815-56-5 |
| 19 | Anionic | Xylene Sulfonates | Sodium Xylene Sulfonate | 1300-72-7 |
| 20 | Cationic | Amine Oxides | Lauramine Oxide | 1643-20-5 |
| 21 | Cationic | Amine Oxides | Cocamidopropylamine Oxide | 68155-09-9 |
| 22 | Cationic | Amine Oxides | Lauryl/Myristyl amidopropyl amine oxide | 61792-31-2 and 67806-10-4 |
| 23 | Cationic | Amine Oxides | tallow amine + 2 EO | 61791-46-6 |
| 24 | Cationic | Amine Oxides | Myristamine Oxide | 3332-27-2 |
| 25 | Cationic | Onium compound | Soyethyl morpholinium ethosulfate | 61791-34-2 |
| 26 | Cationic | Quaternized Ammonium Compound | Dioleyloylethyl hydroxyethylmonium methosulfate | 94095-35-9 |
| 27 | Cationic | Quaternized Ammonium Compound | Quaternium 18 (Distearyl Dimethyl Ammonium Chloride) | 61789-80-8 |
| 28 | Cationic | Quaternized Ammonium Compound | Alkyl Dimethyl Benzyl Ammonium Chloride | 68424-85-1 |
| 29 | Cationic | Quaternized Ammonium Compound | Quaternium 12 (Didecyl Dimethyl Ammonium Chloride) | 7173-51-5 |
| 30 | Cationic | Quaternized Ammonium Compound | Dialkyl dimethyl ammonium chloride | 68424-95-3 |
| 31 | Amphoteric | Betaine | Cocamidopropyl Betaine | 61789-40-0 |
| 32 | Amphoteric | Betaine | Cetyl Betaine | 693-33-4 and 683-10-3 |
| 33 | Amphoteric | Betaine | Lauramidopropyl Betaine | 4292-10-8 |
| 34 | Amphoteric | Imidazolium compound | Disodium Cocoamphodipropionate | 68604-71-7 |
| 35 | Amphoteric | Imidazolium compound | Disodium Cocoamphodiacetate | 68650-39-5 |
| 36 | Amphoteric | Imidazolium compound | Sodium Cocoamphoacetate | 68608-65-1 |
| 37 | Amphoteric | Sultaine | Lauryl Hydroxysultaine | 13197-76-7 |
| 38 | Nonionic | Alcohol Ethoxylates | Linear alcohol (C11) ethoxylate, POE-7 | 34398-01-1 |
| 39 | Nonionic | Alcohol Ethoxylates | Linear alcohol (C9-11) ethoxylate, POE-2.5 | 68439-46-3 |
| 40 | Nonionic | Alcohol Ethoxylates | Lauryl alcohol ethoxylate, POE-8 | 9002-92-0 |
| 41 | Nonionic | Alcohol Ethoxylates | Secondary Alcohol Ethoxylates | 84133-50-7 |
| 42 | Nonionic | Alkanolamides | Trideceth-2 Carboxamide MEA | 107628-04-6 |
| 43 | Nonionic | Alkanolamides | PEG-4 Rapeseedamide | 85536-23-8 |
| 44 | Nonionic | Alkanolamides | PEG 5 Cocamide | 68425-44-5 |
| 45 | Nonionic | Alkanolamides | Cocamide DEA | 68603-42-9 |
| 46 | Nonionic | Alkanolamides | Lauramide MEA | 142-78-9 |
| 47 | Nonionic | Alkanolamides | Cocamide MEA | 68140-00-1 |
| 48 | Nonionic | Alkanolamides | Lauramide DEA | 120-40-1 |
| 49 | Nonionic | Alkanolamides | Oleamide DEA | 93-83-4 |
| 50 | Nonionic | Alkyl polyglycosides | Caprylyl/Myristyl Glucosid | 68515-73-1 and 110615-47-9 |
| 51 | Nonionic | Alkyl polyglycosides | Lauryl/Myristyl Glucosid | 110615-47-9 |
| 52 | Nonionic | Alkyl polyglycosides | Caprylyl/Decyl Glucoside | 68515-73-1 |

TABLE 2-continued

Surfactants tested in compositions 1 to 68

| # | Type | Chemical group | INCI Name | # CAS |
|---|---|---|---|---|
| 53 | Nonionic | Amide | N,N-Dimethyldecanamide | 14433-76-2 |
| 54 | Nonionic | Biosurfactant | Sophorolipid | — |
| 55 | Nonionic | Esters | Isopropyl Myristate | 110-27-0 |
| 56 | Nonionic | Esters | Isopropyl Palmitate | 142-91-6 |
| 57 | Nonionic | Fatty acid, natural origin | Glycereth-17 Cocoate | 68201-46-7 |
| 58 | Nonionic | Fatty acid, natural origin | Glycereth-6 Cocoate | 68201-46-7 |
| 59 | Nonionic | Fatty acid, natural origin | PEG/PPG-6/2 Glyceryl cocoate | 72245-11-5 |
| 60 | Nonionic | Fatty Alcohol | Cetostearyl Alcohol | 67762-27-0 |
| 61 | Nonionic | Fatty Amine Ethoxylate | PEG 2 Cocamine | 61791-14-8 |
| 62 | Nonionic | Fatty Amine Ethoxylate | PEG 2 Tallow Amine | 61791-26-2 |
| 63 | Nonionic | Glycerol ester | Glycereth-7 Caprylate/Caprate | 36145938-3 |
| 64 | Nonionic | Glycerol ester | caprylic/capric triglyceride | 73398-61-5 |
| 65 | Nonionic | Glycerol ester | Glyceryl oleate | 37220-82-9 |
| 66 | Nonionic | Glycerol ester | Glyceryl stearate | 123-94-4 |
| 67 | Nonionic | Lactate | Lauryl Lactyl Lactate | 910661-93-7 |
| 68 | Nonionic | Sorbitan Ester | Polysorbate 80 | 9005-65-6 |

Antimicrobial Efficacy Test 0.1 mL of bacterial culture containing *Staphylococcus aureus* is inoculated in a tube containing 10 mL of a given composition. The content of the tube is then mixed and left to stand for 2 minutes (the "contact time"). After 2 minutes, 0.01 mL of tube content is transferred to a tube containing 9 mL of a neutralizing bacterial culture media (Letheen Broth) that stops the antimicrobial action of the composition and allows microbial growth. Tubes are then checked for presence of microbial growth after 72 h. For each antimicrobial efficacy test, the plating of positive controls followed by colony counting was done to establish the log reduction of *S. aureus* as a result of 2 minutes contact with compositions 1-68. If no growth is observed in the tested tube, the composition is considered to kill at least the bacterial load of the positive control.

Table 3 presents the results of the efficacy tests for compositions 1-68. The Log reduction of *S. aureus* is indicated for each composition. Each composition is formulated with the different surfactants at a concentration of 0.12 and/or 0.35% weight.

TABLE 3

Antimicrobial efficacy results against *Staphylococcus aureus*.

| | Composition | Surfactant at 0.35% (w/w) Log reduction | Surfactant at 0.12% (w/w) Log reduction |
|---|---|---|---|
| Anionic | 1 | >7.98 | >5.84 |
| | 2 | >5.04 | >5.84 |
| | 3 | >5.04 | N/A |
| | 4 | >7.98 | N/A |
| | 5 | >5.51 | >5.64 |
| | 6 | >5.76 | >5.64 |
| | 7 | >5.76 | >5.64 |
| | 8 | >5.76 | >5.64 |
| | 9 | >7.98 | >5.84 |
| | 10 | >7.98 | >5.84 |
| | 11 | >5.04 | >5.64 |
| | 12 | >5.04 | >5.64 |
| | 13 | >5.04 | >5.64 |
| | 14 | >5.04 | >5.64 |
| | 15 | >7.98 | N/A |

TABLE 3-continued

Antimicrobial efficacy results against *Staphylococcus aureus*.

| | Composition | Surfactant at 0.35% (w/w) Log reduction | Surfactant at 0.12% (w/w) Log reduction |
|---|---|---|---|
| | 16 | >7.98 | >5.84 |
| | 17 | >7.98 | N/A |
| | 18 | >5.04 | >5.64 |
| | 19 | >5.04 | >5.64 |
| Cationic | 20 | >4.43 | N/A |
| | 21 | >4.43 | >5.64 |
| | 22 | >5.72 | >5.64 |
| | 23 | >4.43 | >5.64 |
| | 24 | N/A | N/A |
| | 25 | >7.98 | N/A |
| | 26 | >5.76 | >5.64 |
| | 27 | N/A | >5.64 |
| | 28 | >5.04 | >5.64 |
| | 29 | >5.04 | >5.64 |
| | 30 | >7.98 | >5.84 |
| Amphoteric | 31 | >5.72 | >5.64 |
| | 32 | >4.43 | >5.64 |
| | 33 | >5.04 | >5.64 |
| | 34 | >5.04 | >5.84 |
| | 35 | >5.04 | >5.64 |
| | 36 | >5.04 | >5.64 |
| | 37 | >5.76 | >5.64 |
| Non-ionic | 38 | >4.43 | >5.64 |
| | 39 | >5.76 | N/A |
| | 40 | N/A | >5.64 |
| | 41 | N/A | >5.64 |
| | 42 | N/A | >5.64 |
| | 43 | >4.43 | >5.84 |
| | 44 | >4.43 | N/A |
| | 45 | >7.98 | >5.84 |
| | 46 | >5.04 | >5.64 |
| | 47 | >4.43 | >5.64 |
| | 48 | N/A | >5.64 |
| | 49 | >4.43 | >5.64 |
| | 50 | >7.98 | >5.84 |
| | 51 | >7.98 | >5.84 |
| | 52 | >7.98 | N/A |
| | 53 | N/A | >5.64 |
| | 54 | >6.43 | >5.64 |
| | 55 | N/A | >5.64 |
| | 56 | N/A | >5.84 |
| | 57 | >4.43 | N/A |

TABLE 3-continued

Antimicrobial efficacy results against *Staphylococcus aureus*.

| Composition | Surfactant at 0.35% (w/w) Log reduction | Surfactant at 0.12% (w/w) Log reduction |
|---|---|---|
| 58 | >5.76 | >5.64 |
| 59 | >4.43 | >5.64 |
| 60 | >4.43 | >5.64 |
| 61 | >5.51 | >5.64 |
| 62 | N/A | >5.64 |
| 63 | >5.76 | >5.64 |
| 64 | >4.43 | >5.64 |
| 65 | >7.98 | >5.84 |
| 66 | N/A | >5.64 |
| 67 | >5.76 | >5.64 |
| 68 | >4.43 | >5.64 |

CONCLUSIONS

Each type of surfactants (anionic, cationic, amphoteric and non-ionic) was tested in the disinfectant formulation of the present invention. Compositions 1-68 covered the different types of surfactants, but also the most common chemical groups of surfactants available on the market. The composition of the present invention therefore can be formulated with any surfactant, while maintaining the antimicrobial efficacy.

From the results found in Table 3, it is clear that compositions 1-68 of the present invention maintain antimicrobial efficacy with a contact time of 2 minutes.

pH adjusting Agent Containing Compositions

Composition of the present invention containing pH adjusting agents are prepared according to the amounts listed below:

Lactic acid

| | Compositions | | | | |
|---|---|---|---|---|---|
| Ingredient (% w/w) | LA 1 | LA 2 | LA 3 | LA 4 | LA 5 |
| Thymol | 23 | 23 | 23 | 23 | 23 |
| Surfactant | 12 | 11.7 | 11.4 | 11.1 | 10.8 |
| Solvent | 36 | 36 | 36 | 36 | 36 |
| Lactic acid solution ≥85% | 1 | 2 | 3 | 4 | 5 |
| Water | QS | QS | QS | QS | QS |
| pH | 3.92 | 3.6 | 3.41 | 3.24 | 3.18 |
| pH 1:100 dilution in water | 5.93 | 4.2 | 3.7 | 3.39 | 3.34 |

Citric acid

| | Compositions | | | | |
|---|---|---|---|---|---|
| Ingredient (% w/w) | CA1 | CA2 | CA3 | CA4 | CA5 |
| Thymol | 23 | 23 | 23 | 23 | 23 |
| Surfactant | 12 | 11.7 | 11.4 | 11.1 | 10.8 |
| Solvent | 36 | 36 | 36 | 36 | 36 |
| Citric acid solution ≥99.5% | 1 | 2 | 3 | 4 | 5 |
| Water | QS | QS | QS | QS | QS |
| pH | 3.34 | 3.00 | 2.81 | 2.64 | 2.50 |
| pH 1:100 dilution in water | 5.46 | 4.19 | 3.60 | 3.20 | 3.16 |

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

What is claimed is:

1. An aqueous disinfectant formulation consisting of:
   a) from about 0.05% to about 25% weight of at least one antimicrobial isolated or synthetic phenolic compound of natural origin selected from the group consisting of thymol and carvacrol;
   b) from about 0.1% to about 15% weight of an anionic, a cationic, an amphoteric, an non-ionic surfactant, or combinations thereof, in an amount sufficient to form a solution or dispersion of said phenolic compound in an aqueous carrier;
   c) from about 0.1% to about 40% weight of a solvent;
   d) from about 0.01% to about 10% weight of a sequestering agent selected from the group consisting of citric acid, sodium citrate, and a combination thereof;
   e) sufficient water to make 100 weight percent.

2. The aqueous disinfectant formulation of claim 1, wherein said solution consists of:
   a) from about 5% to about 25% weight percent of said phenolic compound;
   b) from about 5% to about 15% weight percent of said surfactant;
   c) from about 5% to about 35% weight of said solvent;
   d) from about 1% to about 5% weight percent of said sequestering agent; and
   e) sufficient water to make 100 weight percent.

3. The aqueous disinfectant formulation of claim 1, wherein said solution consists of:
   a) from about 15% to about 25% weight of said phenolic compound;
   b) from about 10% to about 15% weight of said surfactant;
   c) from about 15% to about 30% weight of said solvent;
   d) from about 1% to about 3% weight of said sequestering agent; and
   e) sufficient water to make 100 weight percent.

4. The aqueous disinfectant formulation of claim 1, wherein said anionic, cationic, amphoteric, non-ionic surfactant is selected from the group consisting of an alpha Sulfo methyl ester surfactant, a diphenyl oxide disulfonate surfactant, a dodecylbenzene sulfonic acid surfactant, a dodecylbenzene sulfonic salt surfactant, an ether carboxylate surfactant, an isethionate surfactant, a lauryl ether sulphate surfactant, a lauryl sulphate surfactant, a phosphate ester surfactant, a phophanate surfactant, a sarcosinate surfactant, a sulfosuccinate surfactant, a xylene sulfonate surfactant, an amine oxide surfactant, an onium compound, a quaternized ammonium compound, a betaine surfactant, an imidazolium compound, a sultaine surfactant, an alcohol ethoxylate surfactant, an alkanolamide surfactant, an alkyl polyglycoside surfactant, an amide surfactant, a biosurfactant, an ester surfactant, a fatty acid of natural origin surfactant, a fatty alcohol surfactant, a fatty amine ethoxylate surfactant, a glycerol ester surfactant, a lactate surfactant, a sorbitan ester surfactant.

5. The aqueous disinfectant formulation of claim 1, wherein said anionic, cationic, amphoteric, non-ionic surfactant is selected from the group consisting of sodium lauryl sulphate, sodium methyl 2-sulfolaurate, disodium 2-sulfolaurate, sodium dodecyl diphenyl ether disulfonate, sodium decyl diphenyl oxide disulfonate, sodium dodecylbenzenesulfonate, dodecylbenzene sulfonic acid, capryleth-9 carboxylic acid, hexeth-4 carboxylic acid, glycolic acid ethoxylate lauryl ether, sodium cocoyl isethionate, sodium lauryl ether sulfate, sodium lauryl sulfate, triethanolamine lauryl sulfate, magnesium lauryl sulfate, nonoxynol 10 phosphate, deceth 4 phosphate, amino tri (methylene phosphonic acid) pentasodium salt (Na5ATMP), 1-Hydroxyethylidene-1,1,-diphosphonic acid (HEDP), sodium lauroyl sarcosinate, sisodium laureth sulfosuccinate, sodium xylene sulfonate, lauramine oxide, cocamidopropylamine oxide, lauryl amidopropyl amine oxide, myristyl amidopropyl amine oxide, tallow amine (2 EO), soyethyl morpholinium ethosulfate, dioleyloylethyl hydroxyethylmonium methosulfate, quaternium 18 (distearyl dimethyl ammonium chloride), alkyl dimethyl benzyl ammonium chloride, quaternium 12 (didecyl dimethyl ammonium chloride), dialkyl dimethyl ammonium chloride, cocamidopropyl betaine, cetyl betaine, lauramidopropyl betaine, disodium cocoamphodipropionate, disodium cocoamphodiacetate, sodium cocoamphoacetate, lauryl hydroxysultaine, linear alcohol ($C_{11}$) ethoxylate-POE—7, linear alcohol ($C_{9-11}$) ethoxylate—POE-2.5, lauryl alcohol ethoxylate—POE-8, secondary alcohol ethoxylates, trideceth-2 carboxamide MEA, PEG-4 Rapeseed amide, PEG 5 Cocamide, cocamide DEA, lauramide MEA, cocamide MEA, lauramide DEA, oleamide DEA, caprylyl glucoside, myristyl glucoside, lauryl glucoside, myristyl glucoside, caprylyl glucoside, decyl glucoside, N,N-dimethyldecanamide, sophorolipid, isopropyl myristate, sopropyl palmitate, glycereth-17 cocoate, glycereth-6 cocoate, PEG/PPG-6/2 glyceryl cocoate, cetostearyl alcohol, PEG 2 cocamine, PEG 2 tallow Amine, glycereth-7 caprylate, glycereth-7 caprate, caprylic triglyceride, capric triglyceride, glyceryl oleate, glyceryl stearate, lauryl lactyl lactate, polysorbate 80 and combinations thereof.

6. The aqueous disinfectant formulation of claim 1, comprising a pH ranging from about 6 to about 9.

7. A method of using the disinfectant formulation of claim 1, comprising the step of diluting the disinfectant formulation with water.

8. A method of disinfecting a surface comprising applying the disinfectant formulation of claim 1 to a surface in need of disinfecting.

9. An aqueous disinfectant formulation consisting of:
  a) from about 0.05% to about 25% weight of at least one antimicrobial isolated or synthetic phenolic compound of natural origin selected from the group consisting of thymol and carvacrol;
  b) from about 0.1% to about 15% weight of an anionic, a cationic, an amphoteric, an non-ionic surfactant, or combinations thereof, in an amount sufficient to form a solution or dispersion of said phenolic compound in an aqueous carrier;
  c) from about 0.1% to about 40% weight of a solvent;
  d) from about 0.01% to about 10% weight of a sequestering agent selected from the group consisting of citric acid, sodium citrate, and a combination thereof;
  at least one of e) and f)
    e) from about 0% to about 4% weight of an essential oil selected from the group consisting of origanum oil, thyme oil, and eucalyptus oil;
    f) from about 0% to about 1.5% weight of a fragrance; and
  g) sufficient water to make 100 weight percent.

10. The aqueous disinfectant formulation of claim 9, wherein said solution consists of:
  a) from about 5% to about 25% weight of said phenolic compound;
  b) from about 5% to about 15% weight of said surfactant;
  c) from about 5% to about 35% weight of said solvent;
  d) from about 1% to about 5% weight of said sequestering agent; at least one of e) and f)
    e) from about 0.04% to about 4% weight of said essential oil;
    f) from about 0.04% to about 1.5% weight of said fragrance; and
  g) sufficient water to make 100 weight percent.

11. The aqueous disinfectant formulation of claim 9, wherein said solution consists of:
  a) from about 15% to about 25% weight of said phenolic compound;
  b) from about 10% to about 15% weight of said surfactant; and
  c) from about 15% to about 30% weight of said solvent;
  d) from about 1% to about 3% weight of said sequestering agent; at least one of e) and f)
    e) from about 0.04% to about 4% weight of said essential oil;
    f) from about 0.04% to about 1.5% weight of said fragrance; and
  g) sufficient water to make 100 weight percent.

12. The aqueous disinfectant formulation of claim 9, wherein said anionic, cationic, amphoteric, non-ionic surfactant is selected from the group consisting of an alpha Sulfo methyl ester surfactant, a diphenyl oxide disulfonate surfactant, a dodecylbenzene sulfonic acid surfactant, a dodecylbenzene sulfonic salt surfactant, an ether carboxylate surfactant, an isethionate surfactant, a lauryl ether sulphate surfactant, a lauryl sulphate surfactant, a phosphate ester surfactant, a phophanate surfactant, a sarcosinate surfactant, a sulfosuccinate surfactant, a xylene sulfonate surfactant, an amine oxide surfactant, an onium compound, a quaternized ammonium compound, a betaine surfactant, an imidazolium compound, a sultaine surfactant, an alcohol ethoxylate surfactant, an alkanolamide surfactant, an alkyl polyglycoside surfactant, an amide surfactant, a biosurfactant, an ester surfactant, a fatty acid of natural origin surfactant, a fatty alcohol surfactant, a fatty amine ethoxylate surfactant, a glycerol ester surfactant, a lactate surfactant, a sorbitan ester surfactant.

13. The aqueous disinfectant formulation of claim 9, wherein said anionic, cationic, amphoteric, non-ionic surfactant is selected from the group consisting of sodium lauryl sulphate, sodium methyl 2-sulfolaurate, disodium 2-sulfolaurate, sodium dodecyl diphenyl ether disulfonate, sodium decyl diphenyl oxide disulfonate, sodium dodecylbenzenesulfonate, dodecylbenzene sulfonic acid, capryleth-9 carboxylic acid, hexeth-4 carboxylic acid, glycolic acid ethoxylate lauryl ether, sodium cocoyl isethionate, sodium lauryl ether sulfate, sodium lauryl sulfate, triethanolamine lauryl sulfate, magnesium lauryl sulfate, nonoxynol 10 phosphate, deceth 4 phosphate, amino tri (methylene phosphonic acid) pentasodium salt (Na5ATMP), 1-Hydroxyethylidene-1,1,-diphosphonic acid (HEDP), sodium lauroyl sarcosinate, sisodium laureth sulfosuccinate, sodium xylene sulfonate, lauramine oxide, cocamidopropylamine oxide, lauryl amidopropyl amine oxide, myristyl amidopropyl amine oxide, tallow amine (2 EO), soyethyl morpholinium ethosulfate, dioleyloylethyl hydroxyethylmonium methosulfate, quaternium 18 (distearyl dimethyl ammonium chloride), alkyl dimethyl benzyl ammonium chloride, quaternium 12 (didecyl dimethyl ammonium chloride), dialkyl dimethyl ammonium chloride, cocamidopropyl betaine, cetyl betaine, lauramidopropyl betaine, disodium cocoamphodipropionate, disodium cocoamphodiacetate, sodium cocoamphoacetate, lauryl hydroxysultaine, linear alcohol ($C_{11}$) ethoxylate—POE-7, linear alcohol ($C_{9-11}$) ethoxylate—POE-2.5, lauryl alcohol ethoxylate—POE-8, secondary alcohol ethoxylates, trideceth-2 carboxamide MEA, PEG-4 Rapeseed amide, PEG 5 Cocamide, cocamide DEA, lauramide MEA, cocamide MEA, lauramide DEA, oleamide DEA, caprylyl glucoside, myristyl glucoside, lauryl glucoside, myristyl glucoside, caprylyl glucoside, decyl glucoside, N,N-dimethyldecanamide, sophorolipid, isopropyl myristate, sopropyl palmitate, glycereth-17 cocoate, glycereth-6 cocoate, PEG/PPG-6/2 glyceryl cocoate, cetostearyl alcohol, PEG 2 cocamine, PEG 2 tallow Amine, glycereth-7 caprylate, glycereth-7 caprate, caprylic triglyceride, capric triglyceride, glyceryl oleate, glyceryl stearate, lauryl lactyl lactate, polysorbate 80 and combinations thereof.

14. The aqueous disinfectant formulation of claim 9, comprising a pH ranging from about 6 to about 9.

15. A method of using the disinfectant formulation of claim 9, comprising the step of diluting the disinfectant formulation with water.

16. A method of disinfecting a surface comprising applying the disinfectant formulation of claim 9 to a surface in need of disinfecting.

17. The aqueous disinfectant formulation of claim 1, comprising a pH ranging from about 1 to about 6.

18. The aqueous disinfectant formulation of claim 9, comprising a pH ranging from about 1 to about 6.

* * * * *